United States Patent [19]
Panescu et al.

[11] Patent Number: 5,792,064
[45] Date of Patent: Aug. 11, 1998

[54] SYSTEMS AND METHODS FOR ANALYZING CARDIAC BIOPOTENTIAL MORPHOLOGIES BY CROSS-CORRELATION

[76] Inventors: Dorin Panescu, 382 N. Fair Oaks, Apt 4, Sunnyvale, Calif. 94086; Michael D. Lesh, 301 Monte Vista Ave., Mill Valley, Calif. 94941; David K. Swanson, 877 Heatherstone Way, Mountain View, Calif. 94040; James G. Whayne, 17930 Los Felice Rd., Saragota, Calif. 95070

[21] Appl. No.: 949,287

[22] Filed: Oct. 21, 1997

Related U.S. Application Data

[63] Continuation of Ser. No. 790,050, Jan. 28, 1997, abandoned, and a continuation of Ser. No. 390,446, Feb. 17, 1995, abandoned.

[51] Int. Cl.$^6$ .................................................. A61B 5/04
[52] U.S. Cl. ....................................................... 600/510
[58] Field of Search .................. 607/122, 9; 600/373, 600/375, 509, 510, 515, 518; 382/209

[56] References Cited

U.S. PATENT DOCUMENTS

| | | | |
|---|---|---|---|
| 4,616,333 | 10/1986 | Simoni | 364/413.05 X |
| 5,311,873 | 5/1994 | Savard et al. | 128/696 |
| 5,391,199 | 2/1995 | Ben-Haim | 607/122 |
| 5,443,489 | 8/1995 | Ben-Haim | 607/122 X |
| 5,450,846 | 9/1995 | Goldreyer | 607/122 X |
| 5,485,849 | 1/1996 | Panescu et al. | 128/696 X |

Primary Examiner—Jeffrey R. Jastrzab
Attorney, Agent, or Firm—Lyon & Lyon LLP

[57] ABSTRACT

An analog or digital processing element and associated method analyses electrograms or electrocardiograms to locate sites potentially appropriate for ablation. The element and method compares a first number of electrogram or electrocardiogram samples recorded over time during a cardiac event of known diagnosis with a second number of paced electrogram or electrocardiogram samples recorded over time. The comparison cross-correlates the first number of electrogram samples with the second number of paced electrogram samples. The element and method generate an output based upon the cross-correlation. The element and method compare the output to a predetermined value to determine whether a pacing site for the paced electrogram or electrocardiogram samples is near to a potential ablation site.

38 Claims, 9 Drawing Sheets

SYSTEMS AND METHODS FOR ANALYZING CARDIAC BIOPOTENTIAL MORPHOLOGIES BY CROSS-CORRELATION

This is a continuation of application(s) Ser. No. 08/790,050 filed on Jan. 28, 1997, now abandoned which is a continuation of application Ser. No. 08/390,446 filed on Feb. 17, 1995, abandoned.

FIELD OF THE INVENTION

The invention relates to systems and methods for pacing and mapping the heart for diagnosis and treatment of cardiac conditions.

BACKGROUND OF THE INVENTION

Normal sinus rhythm of the heart begins with the sinoatrial node (or "SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node (or "AV node") and the bundle of HIS (or "HIS bundle") to myocardial tissue cells of the ventricles. The depolarization of these cells propagates across the ventricles, causing the ventricles to contract.

This conduction system results in the described, organized sequence of myocardial contraction leading to a normal heartbeat.

Sometimes aberrant conductive pathways develop in heart tissue, which disrupt the normal path of depolarization events. For example, anatomical obstacles in the atria or ventricles can disrupt the normal propagation of electrical impulses. These anatomical obstacles (called "conduction blocks") can cause the electrical impulse to degenerate into several circular wavelets that circulate about the obstacles. These wavelets, called "reentry circuits," disrupt the normal activation of the atria or ventricles. As a further example, localized regions of ischemic myocardial tissue may propagate depolarization events slower than normal myocardial tissue. The ischemic region, also called a "slow conduction zone," creates errant, circular propagation patterns, called "circus motion." The circus motion also disrupts the normal depolarization patterns, thereby disrupting the normal contraction of heart tissue.

The aberrant conductive pathways create abnormal, irregular, and sometimes life-threatening heart rhythms, called arrhythmias. An arrhythmia can take place in the atria, for example, as in atrial tachycardia (AT) or atrial flutter (AF). The arrhythmia can also take place in the ventricle, for example, as in ventricular tachycardia (VT).

In treating arrhythmias, it is essential that the location of the sources of the aberrant pathways (called arrhthymia substrate) be located. Once located, the tissue in the arrthymia substrate can be destroyed, or ablated, by heat, chemicals, or other means. Ablation can remove the aberrant conductive pathway, restoring normal myocardial contraction.

Today, physicians examine the propagation of electrical impulses in heart tissue to locate the arrhthymia substrate. The techniques used to analyze the substrate, commonly called "mapping," identify regions in the heart tissue, which can be ablated or otherwise altered, such as by injection of cells or genes, to treat the arrhythmia.

One form of conventional cardiac tissue mapping techniques uses multiple electrodes positioned in contact with epicardial heart tissue to obtain multiple electrograms. The physician stimulates myocardial tissue by introducing pacing signals and visually observes the morphologies of the electrograms recorded during pacing, which this Specification will refer to as "paced electrograms." The physician visually compares the patterns of paced electrograms to those previously recorded during an arrhythmia episode to locate tissue regions appropriate for ablation. These conventional mapping techniques require invasive open heart surgical techniques to position the electrodes on the epicardial surface of the heart.

Conventional epicardial electrogram processing techniques used for detecting local electrical events in heart tissue are often unable to interpret electrograms with multiple morphologies. Such electrograms are encountered, for example, when mapping a heart undergoing ventricular tachycardia (VT). For this and other reasons, consistently high correct foci identification rates (CIR) cannot be achieved with current multi-electrode mapping technologies.

Another form of conventional cardiac tissue mapping technique, called pace mapping, uses a roving electrode in a heart chamber for pacing the heart at various endocardial locations. In searching for the VT foci, the physician must visually compare all paced electrocardiograms (recorded by twelve lead body surface electrocardiograms (ECG's)) to those previously recorded during an induced VT. The physician must constantly relocate the roving electrode to a new location to systematically map the endocardium.

These techniques are complicated and time consuming. They require repeated manipulation and movement of the pacing electrodes. At the same time, they require the physician to visually assimilate and interpret the electrocardiograms.

There thus remains a real need for cardiac mapping and ablation systems and procedures that simplify and automate the analysis of electrograms and the use of electrograms to locate appropriate arrhythmogenic substrate.

SUMMARY OF THE INVENTION

A principal objective of the invention is to provide improved probes and methodologies to examine heart tissue morphology quickly and accurately.

The invention provides systems and methods for determining appropriate ablation sites by comparing electrograms obtained during an arrhythmia episode to those obtained during pacing and mapping.

One aspect of the invention provides an analog or digital processing element and associated method for analyzing electrograms. The element and method input a first number of electrogram samples over time during a cardiac event of known diagnosis, such as, for example, VT or AT. The element and method also input a second number of paced electrogram samples over time. The element and method cross-correlate the first number of event-specific electrogram samples with the second number of paced electrogram samples. The element and method generate an output based upon the cross-correlation. The output aids in identifying potentially appropriate tissue sites for ablation.

In a preferred embodiment, the element and method use an array of multiple electrodes supported within a heart chamber in operative association with a region of endocardial tissue. The element and method condition the electrode array to record at each electrode a first number of electrogram samples over time during the cardiac event of known diagnosis. The element also sequentially conditions different ones of the multiple electrodes on the array to emit a pacing signal and to record at each electrode on the array a second number of paced electrogram samples over time. In this implementation, the element and method individually cross-correlate. for each different one of the pacing signal-emitting electrodes, the first number of event-specific electrogram samples with the second number of paced electrogram samples. The element and method generate an output for each electrode on the array.

In a preferred embodiment, the output comprises a numerical set of cross-correlation functions.

Another aspect of the invention provides an analog or digital element and associated method for analyzing electrocardiograms. The element and associated method input a first number of electrocardiogram samples recorded over time during a cardiac event of known diagnosis using multiple body surface electrodes. The element and method also input a second number of paced electrocardiogram samples recorded over time using the multiple body surface electrodes. The element and method cross-correlate the first number of event-specific electrocardiogram samples with the second number of paced electrocardiogram samples and generate an output based upon the cross-correlation. The output aids in identifying site or sites potentially appropriate for ablation.

In a preferred embodiment, the output comprises a numerical cross-correlation function.

Other features and advantages of the inventions are set forth in the following Description and Drawings, as well as in the appended Claims.

The invention may be embodied in several forms without departing from its spirit or essential characteristics. The scope of the invention is defined in the appended claims. rather than in the specific description preceding them. All embodiments that fall within the meaning and range of equivalency of the claims are therefore intended to be embraced by the claims.

DESCRIPTION OF THE PREFERRED EMBODIMENTS

Figure 1A:
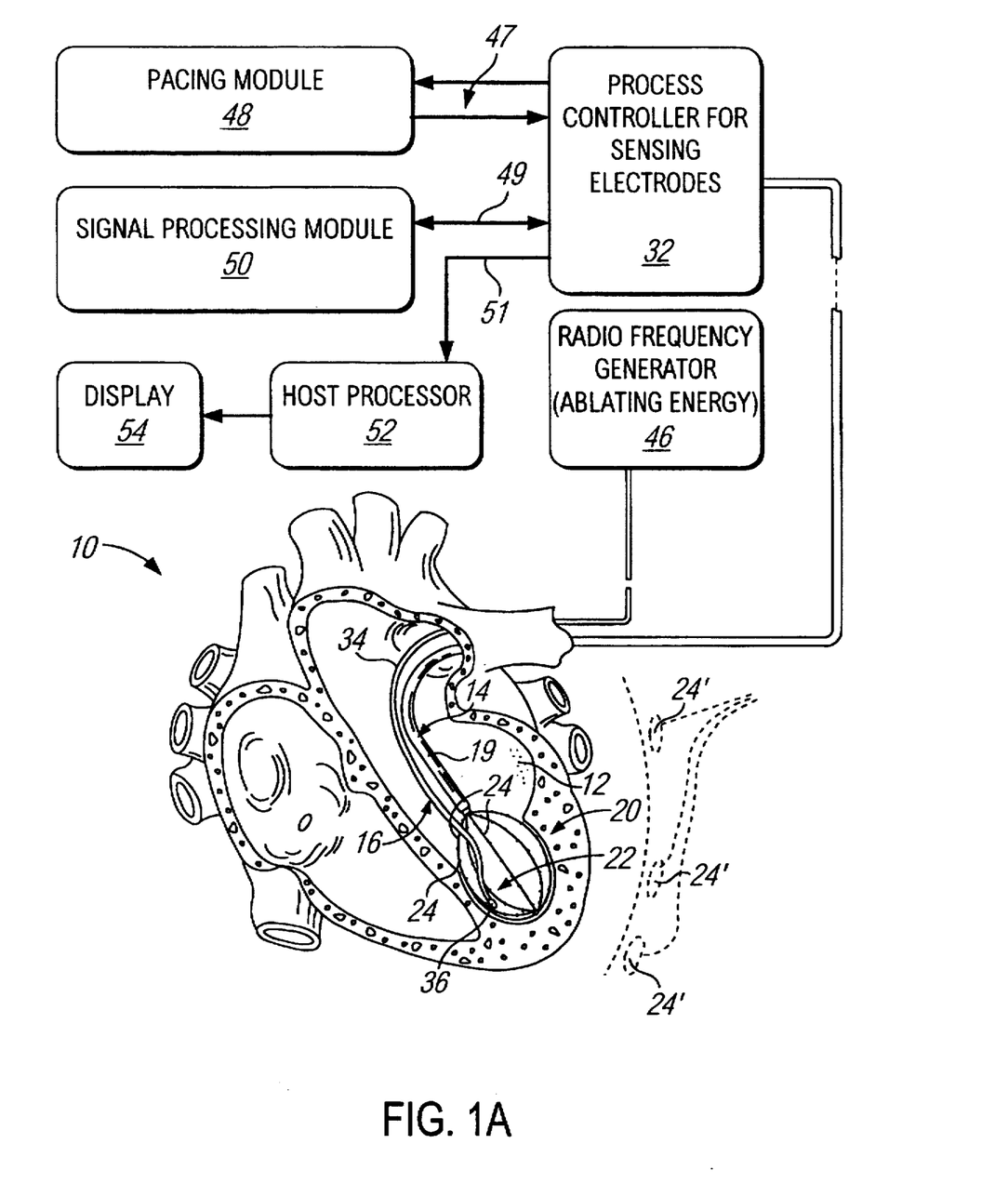
FIG. 1A is a diagrammatic view of a system, which embodies the features of the invention, for accessing a targeted tissue region in the body for diagnostic or therapeutic purposes.

FIG. 1A shows the components of a system 10 for analyzing body tissue biopotential morphologies for diagnostic or therapeutic purposes. The illustrated embodiment shows the system 10 being used to examine the depolarization of heart tissue that is subject to an arrhythmia. In this embodiment, the system 10 serves to locate an arrhythmogenic substrate for removal by ablation. The invention is well suited for use in conducting electrical therapy of the heart.

Still, it should be appreciated that the invention is applicable for use in other regions of the body where tissue biopotential morphologies can be ascertained by analyzing electrical events in the tissue. For example, the various aspects of the invention have application in procedures for analyzing brain or neurologic tissue.

FIG. 1A shows the system 10 analyzing endocardial electrical events. using catheter-based, vascular access techniques. Still. many aspects of the invention can be used in association with techniques that do not require any intrusion into the body. like surface electrocardiograms or electroencephalograms. Many of the aspects of the invention also can be used with invasive surgical techniques. like in open chest or open heart surgery, or during brain surgery.

Figure 1B:
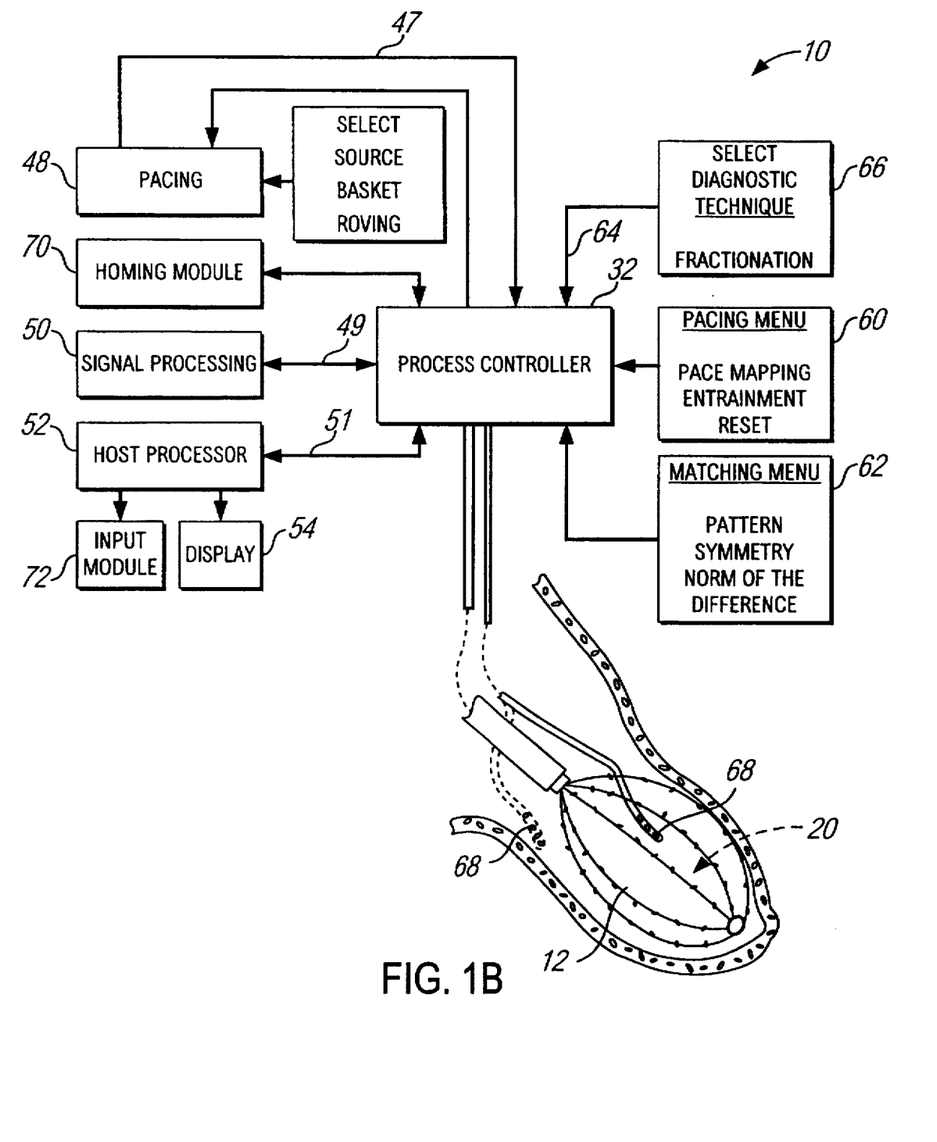
FIG. 1B is a diagrammatic view of the system shown in FIG. 1A, with the inclusion of a roving pacing probe and additional features to aid the physician in conducting diagnosis and therapeutic techniques according to the invention.

In particular, FIG. 1A shows the system 10 analyzing electrical events within a selected region 12 inside a human heart. FIGS. 1A and 1B generally show the system 10 deployed in the left ventricle of the heart. Of course, the system 10 can be deployed in other regions of the heart, too. It should also be noted that the heart shown in the FIG. 1 is not anatomically accurate. FIGS. 1A and 1B show the heart in diagrammatic form to demonstrate the features of the invention.

The system 10 includes a mapping probe 14 and an ablation probe 16. In FIG. 1A, each is separately introduced into the selected heart region 12 through a vein or artery (typically the femoral vein or artery) through suitable percutaneous access. Alternatively, the mapping probe 14 and ablation probe 16 can be assembled in an integrated structure for simultaneous introduction and deployment in the heart region 12.

Further details of the deployment and structures of the probes 14 and 16 are set forth in pending U.S. patent application Ser. No. 08/033,641, filed Mar. 16, 1993, entitled "Systems and Methods Using Guide Sheaths for Introducing, Deploying, and Stabilizing Cardiac Mapping and Ablation Probes."

The mapping probe 14 has a flexible catheter body 18. The distal end of the catheteribody 18 carries a three dimensional multiple-electrode structure 20. In the illustrated embodiment, the structure 20 takes the form of a basket defining an open interior space 22 (see FIG. 2). It should be appreciated that other three dimensional structures, or one dimensional or two dimensional arrays, could also be used.

Figure 2:
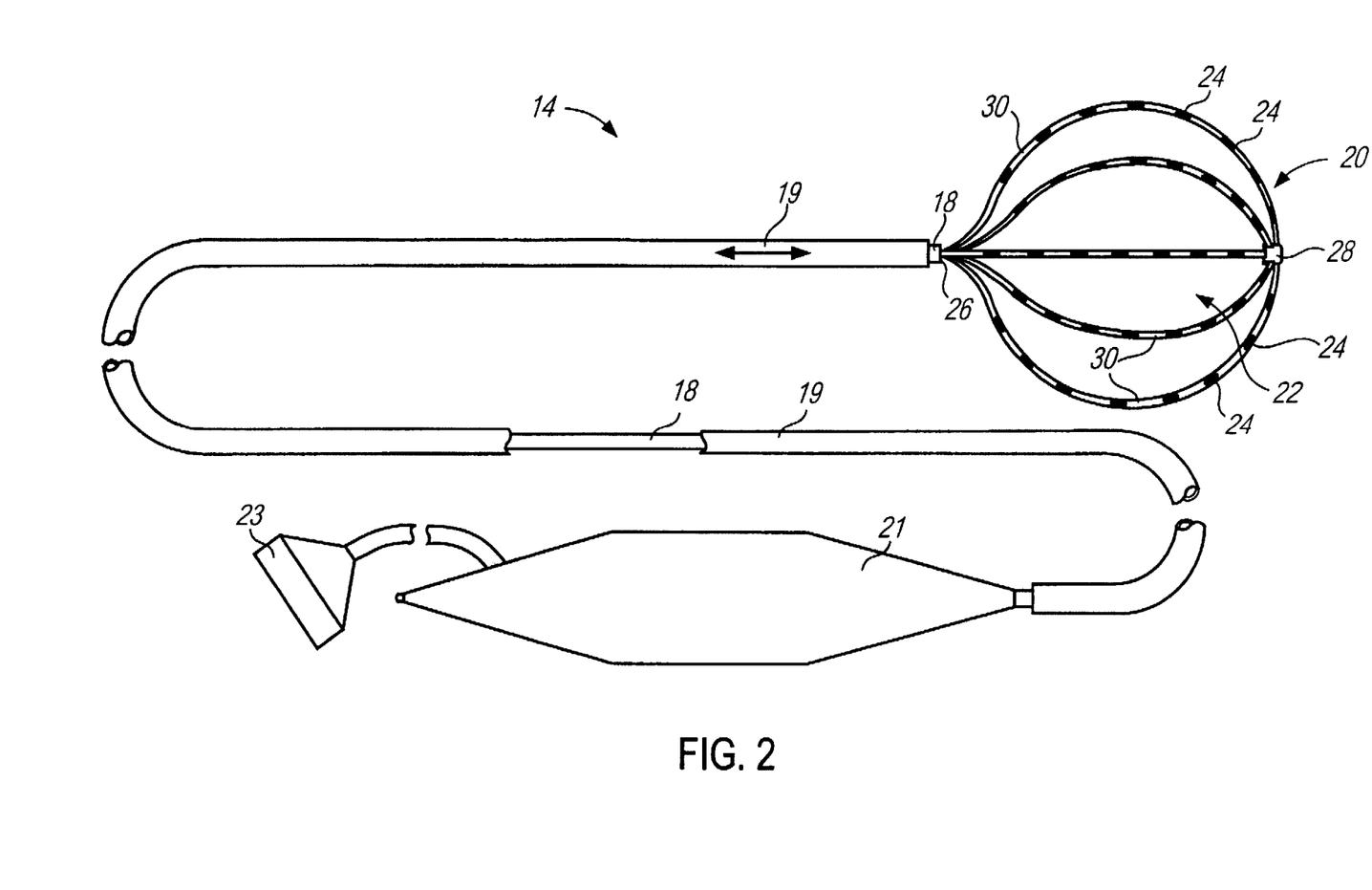
FIG. 2 is an enlarged perspective view of a multiple-electrode structure used in association with the system shown in FIG. 1.

As FIG. 2 shows, the illustrated basket structure 20 comprises a base member 26 and an end cap 28. Generally flexible splines 30 extend in a circumferentially spaced relationship between the base member 26 and the end cap 28.

The splines 30 are preferably made of a resilient, biologically inert material, like Nitinol metal or silicone rubber. The splines 30 are connected between the base member 26 and the end cap 28 in a resilient, pretensed, radially expanded condition, to bend and conform to the endocardial tissue surface they contact. In the illustrated embodiment (see FIG. 2), eight splines 30 form the basket structure 20. Additional or fewer splines 30 could be used.

The splines 30 carry an array of electrodes 24. In the illustrated embodiment, each spline 30 carries eight electrodes 24. Of course, additional or fewer electrodes 24 can be used. Similary, surface electrodes 24' also be used.

A slidable sheath 19 is movable along the axis of the catheter body 18 (shown by arrows in FIG. 2). Moving the sheath 19 forward causes it to move over the basket structure 20, collapsing it into a compact, low profile condition for introducing into the heart region 12. Moving the sheath 19 rearward frees the basket structure 20, allowing it to spring open and assume the pretensed, radially expanded position shown in FIG. 2. The electrodes are urged into contact against the surrounding heart tissue.

Further details of the basket structure are disclosed in pending U.S. patent application Ser. No. 08/206,414, filed Mar. 4, 1994, entitled "Multiple Electrode Support Structures."

In use, the electrodes 24 sense electrical events in myocardial tissue for the creation of electrograms. The electrodes 24 are electrically coupled to a process controller 32 (see FIG. 1A). A signal wire (not shown) is electrically coupled to each electrode 24. The wires extend through the body 18 of the probe 14 into a handle 21, in which they are coupled to an external multiple pin connector 23. The connector 23 electrically couples the electrodes to the process controller 32.

Alternatively, multiple electrode structures can be located epicardially using a set of catheters individually introduced through the coronary vasculature (e.g., retrograde through the aorta or coronary sinus), as disclosed in PCT/US94/01055 entitled "Multiple Intravascular Sensing Devices for Electrical Activity."

Figure 3:
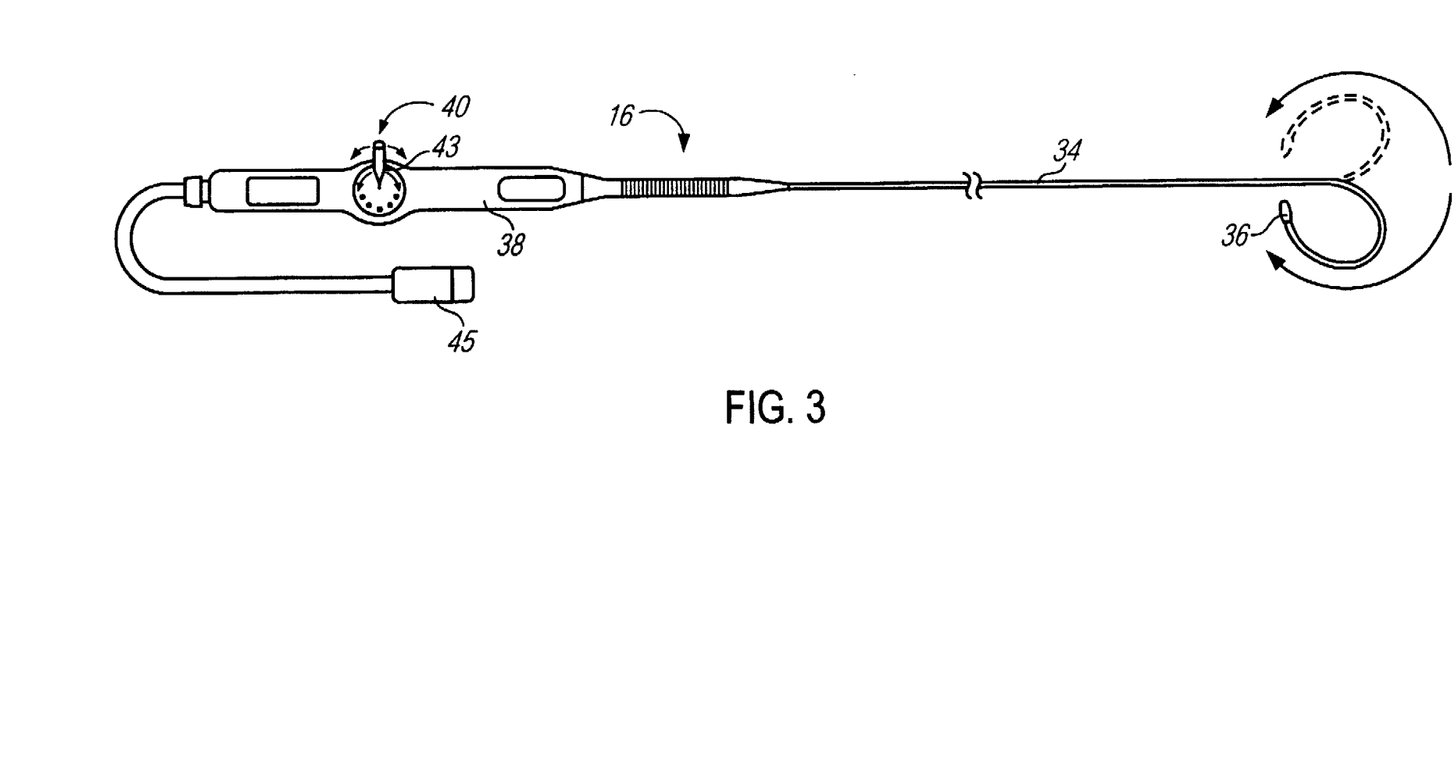
FIG. 3 is an enlarged view of an ablation probe usable in association with the system shown in FIGS. 1A and 1B.

The ablation probe 16 (see FIG. 3) includes a flexible catheter body 34 that carries one or more ablation electrodes 36. For the sake of illustration, FIG. 3 shows a single ablation electrode 36 carried at the distal tip of the catheter body 34. Of course, other configurations employing multiple ablation electrodes are possible, as described in pending U.S. patent application Ser. No. 08/287,310, filed Aug. 8, 1994, entitled "Systems and Methods for Ablating Heart Tissue Using Multiple Electrode Elements."

A handle 38 is attached to the proximal end of the catheter body 34. The handle 38 and catheter body 34 carry a steering mechanism 40 for selectively bending or flexing the catheter body 34 along its length, as the arrows in FIG. 3 show.

The steering mechanism 40 can vary. For example, the steering mechanism can be as shown in U.S. Pat. No. 5,254,088, which is incorporated herein by reference.

A wire (not shown) electrically connected to the ablation electrode 36 extends through the catheter body 34 into the handle 38, where it is electrically coupled to an external connector 45. The connector 45 connects the electrode 36 to a generator 46 of ablation energy. The type of energy used for ablation can vary. Typically, the generator 46 supplies electromagnetic radio frequency energy, which the electrode 36 emits into tissue. A radio frequency generator Model EPT-1000, available from EP Technologies, Inc., Sunnyvale, Calif., can be used for this purpose. Alternatively, genes or cells could be injected to improve conduction.

In use, the physician places the ablation electrode 36 in contact with heart tissue at the site identified for ablation. The ablation electrode emits ablating energy to heat and thermally destroy the contacted tissue.

According to the features of the invention, the process controller 32 employs electrogram cross-correlation to automatically locate for the physician the site or sites potentially appropriate for ablation.

I. Electrogram Cross-Correlation

The process controller 32 is operable to sense electrical events in heart tissue and to process and analyze these events to achieve the objectives of the invention. The process controller 32 is also selectively operable to induce electrical events by transmitting pacing signals into heart tissue.

More particularly, the process controller 32 is electrically coupled by a bus 47 to a pacing module 48, which paces the heart sequentially through individual or pairs of electrodes to induce depolarization. Details of the process controller 32 and pacing module 48 are described in copending U.S. patent application Ser. No. 08/188,316, filed Jan. 28, 1994, and entitled "Systems and Methods for Deriving Electrical Characteristics of Cardiac Tissue for Output in Iso-Characteristic Displays."

The process controller 32 is also electrically coupled by a bus 49 to a signal processing module 50. The processing module 50 processes cardiac signals into electrograms. A Model TMS 320C31 processor available from Spectrum Signal Processing, Inc. can be used for this purpose.

The process controller 32 is further electrically coupled by a bus 51 to a host processor 52, which processes the input from the electrogram processing module 50 in accordance with the invention to locate arrhythmogenic substrate. The host processor 32 can comprise a 486-type microprocessor.

According to the invention, the process controller 32 operates in two functional modes, called the sampling mode and the cross-correlation mode.

In the sampling mode, the physician deploys the basket structure 20 in the desired heart region 12. To assure adequate contact is made in the desired region 12, the physician may have to collapse the basket structure 20, rotate it, and then free the basket structure 20. The degree of contact can be sensed by the process controller 32 in various ways. For example, the process controller 32 can condition the pacing module 48 to emit pacing signals through a selected electrode 24 or pair of electrodes 24. The process controller 32 conditions the electrodes 24 and processing module 50 to detect electrograms sensed by a desired number of the electrodes 24. The processing module can also ascertain the desired degree of contact by measuring tissue impedance, as described in copending patent application Ser. No. 08/221,347, filed Mar. 31, 1994, and entitled "Systems and Methods for Positioning Multiple Electrode Structures in Electrical Contact with the Myocardium."

Once the basket structure 20 is properly positioned, the process controller 32 conditions the electrodes 24 and signal processing module 50 to record electrogram samples during a selected cardiac event having a known diagnosis. In the sampling mode, the process controller 32 typically must condition the pacing module 48 to pace the heart until the desired cardiac event is induced. Of course, if the patient spontaneously experiences the cardiac event while the structure 20 is positioned, then paced-induction is not required.

The processor controller 32 saves these electrogram samples in the host processor 52. At the end of the sampling mode, the process controller 32 typically must condition the pacing module 48 to pace terminate the cardiac event, or the physician may apply a shock to restore normal sinus rhythm.

The cross-correlation mode is begun without altering the position of the multiple electrode structure 20 in the heart region 12, so that the electrodes 24 occupy the same position during the cross-correlation mode as they did during the sampling mode.

In the cross-correlation mode, the process controller 32 first conditions the pacing module 48 to pace the heart in a prescribed manner without inducing the cardiac event of interest, while conditioning the signal processing module 50 to record a number of the resulting electrograms. The process controller 32 then operates the host processor 52 to cross-correlate all or a selected number of the resulting paced electrogram samples to all or a selected number of the electrogram samples collected during the sampling mode. Based upon this comparison, the host processor 52 generates an output that identifies the location of the electrode or electrodes 24 on the structure 20 that are close to a potential ablation site.

A. The Sampling Mode

As before generally described, the process controller 32 operates in the sampling mode while the heart is experiencing a selected cardiac event of known diagnosis and the basket structure 20 is retained in a fixed location in the region 12. In the illustrated and preferred embodiment, the selected event comprises an arrhythmia that the physician seeks to treat, for example, ventricular tachycardia (VT), or atrial tachycardia (AT), or atrial fibrillation (AF).

Figure 4A:
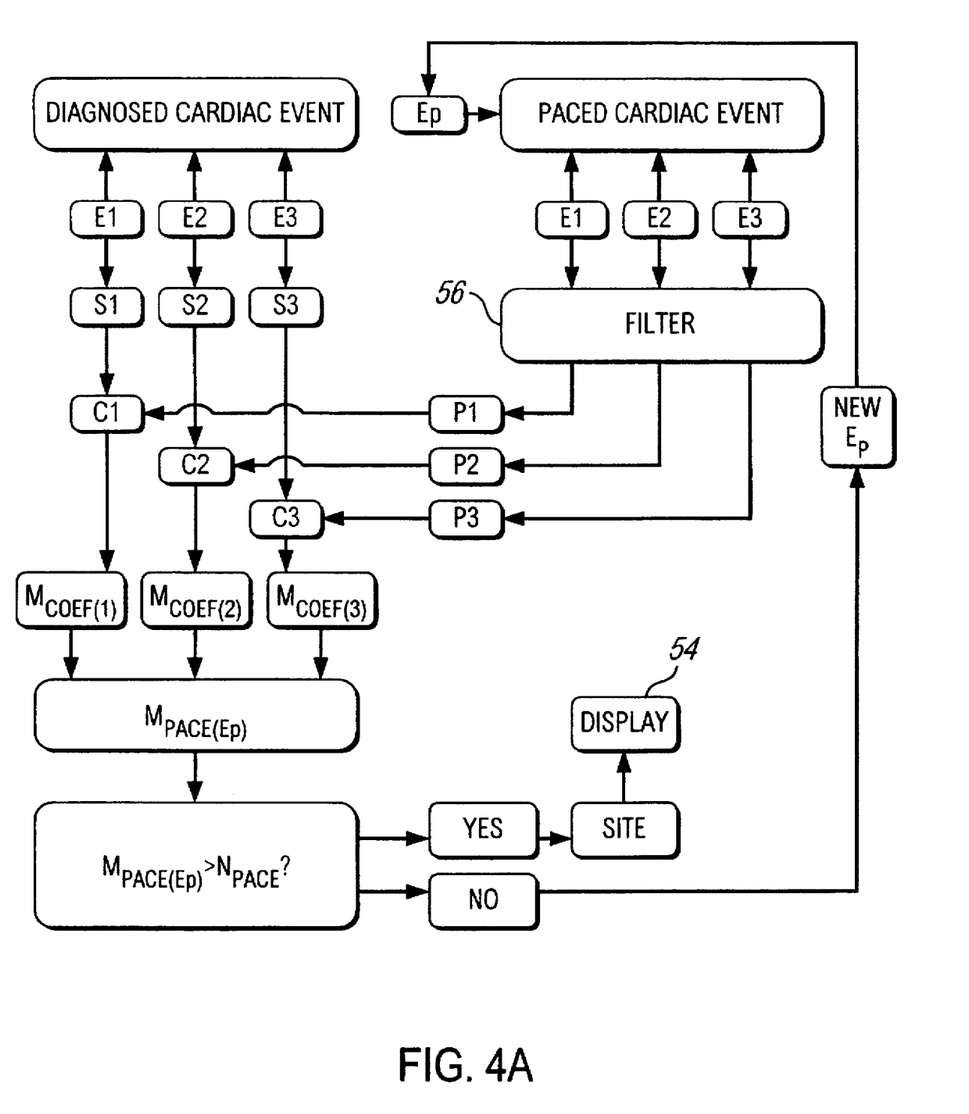
FIG. 4A is a diagrammatic view of the process controller shown in FIGS. 1A and 1B, which locates by electrogram matching a site appropriate for ablation.

As FIG. 4A shows, during the sampling mode, the signal processing module 50 processes a selected number of event-specific electrogram samples obtained from each electrode during the known cardiac event (designated for the purpose of illustration as E1 to E3 in FIG. 4A). The event-specific electrogram samples (designated for the purpose of illustration in FIG. 4A as S1 to S3) may be recorded unipolar (between an electrode 24 and a reference electrode, not shown) or bipolar (between electrodes 24 on the structure 20). The samples S1 to S3 can comprise one heart beat or a specified number of heart beats. Multiple beats may be averaged to reduce noise, if desired.

The host processor 52 retains the set of event-specific electrogram samples Si to S3 in memory. The processor 52 can, for an individual patient, retain sets of event-specific electrogram samples for different cardiac events. For example, a patient may undergo different VT episodes, each with a different morphology. The processor 52 can automatically detect different VT morphologies and store samples for each VT episode for analysis according to the invention. The samples can be downloaded to external disk memory for off-line cross-correlation at a subsequent time, as will be described later.

B. The Cross-Correlation Mode

In the cross-correlation mode, the process controller 32 operates the pacing module 48 to apply pacing signals sequentially to each of the individual electrodes. The pacing electrode is designated Ep in FIG. 4A.

The pacing signal induces depolarization, emanating at the location of the pacing electrode Ep. The process controller 32 operates the signal processing module 50 to process the resulting paced electrogram samples sensed at each electrode (again designated E1 to E3 for the purpose of illustration in FIG. 4A) during pacing by the selected individual electrode Ep. The processed paced electrogram samples are designated P1 to P3 in FIG. 4A.

The paced morphology P1 to P3 at each electrode can be from one heart beat or a specified number of heart beats, provided that the length of the morphologies P1 to P3 are not shorter than the length of the event-specific samples Si to S3 for the same electrodes E1 to E3 obtained during the sampling mode.

Different conventional pacing techniques can be used to obtain the paced morphologies P1 to P3. For example, conventional pace mapping can be used, during which the pace rate is near the arrhythmia rate, but arrhythmia is not induced.

For reasons that will be explained later, conventional entrainment or reset pacing is the preferred technique. During entrainment pacing, the pacing rate is slightly higher than and the period slightly lower than that observed during the arrhythmia event, thereby increasing the rate of the induced arrhythmia event. Further details of entrainment pacing are found in Almendral et al., "Entrainment of Ventricular Tachycardia: Explanation for Surface Electrocardiographic Phenomena by Analysis of Electrograms Recorded Within the Tachy-cardia Circuit," *Circulation*, vol. 77, No. 3, March 1988, pages 569 to 580, which is incorporated herein by reference.

Regardless of the particular pacing technique used, the pacing stimulus may be monophasic, biphasic, or triphasic.

In the cross-correlation mode, while pacing at an individual one of the electrodes Ep, the host processor 52 cross-correlates the paced morphology P1 to P3 obtained at each electrode E1 to E3 to the event-specific samples SI to S3 for the same electrode E1 to E3. The cross-correlations are designated C1 to C3 in FIG. 4A.

Alternatively, the paced morphologies P1 to P3 can be retained in memory or downloaded to external disk memory for cross-correlation at a later time. To accommodate off-line processing, the host processor 52 preferably includes an input module 72 for uploading pregenerated event-specific samples and/or paced samples recorded at an earlier time. The input module 72 allows event specific samples and paced morphologies to be cross-correlated off-line by the host processor 52, without requiring the real time presence of the patient. Alternatively, recorded paced samples can be cross-correlated in real time using event-specific samples generated earlier.

For each pacing electrode Ep(j), the host processor 52 preferably generates a cross-correlation coefficient $M_{COEF(i)}$ for each electrode E(i) from the comparison C(i) of the pacing morphology P(i) to the event-specific morphology S(i) for the same electrode E(i). Preferably, both j and i=1 to n, where n is the total number of electrodes on the three dimensional structure (which, for the purpose of illustration in FIG. 4A, is 3).

The value of the cross-correlation coefficient $M_{COEF(i)}$ is indicative for that electrode E(i) how alike the pacing morphology P(i) is to the event-specific sample S(i) for that electrode E(i). The value of $M_{COEF(i)}$ for each electrode E(i) varies as the location of the pacing electrode Ep(j) changes. Generally speaking, the value of the cross-correlation coefficient $M_{COEF(i)}$ for a given electrode E(i) increases in relation to the closeness of the pacing electrode Ep(j) to the arrhythmogenic foci.

In the illustrated and preferred embodiment (as FIG. 4A shows), while pacing at an individual one of the electrodes Ep(j), the host processor 52 generates from the cross-correlation coefficients $M_{COEF(i)}$ for each electrode E(i) an overall cross-correlation factor $M_{PACE(j)}$ for the pacing electrode Ep(j). The value of the overall cross-correlation factor $M_{PACE(i)}$ for the pacing electrode Ep(j) is indicative of how alike the overall propagation pattern observed during pacing at the electrode Ep(j) is to the overall propagation pattern recorded on the associated event-specific samples.

The process controller 32 operates the pacing module 48 to apply a pacing signal sequentially to each electrode Ep(j) and processes and compares the resulting electrogram morphologies at each electrode E(i) (including Ep(j)) to the event-specific samples, obtaining the cross-correlation coefficients $M_{COEF(i)}$ for each electrode E(i) and an overall cross-correlation factor $M_{PACE(j)}$ for the pacing electrode Ep(j), and so on, until every electrode E(i) serves as a pacing electrode Ep(j).

$M_{PACE(j)}$ for each pacing electrode can be derived from associated cross-correlation coefficients $M_{COEF}$ (i) in various ways.

For example, various conventional averaging techniques can be used. For example, $M_{PACE(j)}$ can be computed as a first order average (arithmetic mean) of $M_{COEF(i)}$ as follows:

$$M_{PACE(j)} = \frac{\Sigma M_{COEF(i)}}{n}$$

where i=1 to n; or as a weighted arithmetic mean, as follows:

$$M_{PACE(ii)} = \Sigma W(i) M_{COEF(i)}$$

where i=1 to n; $\Sigma W(i)=1$. If W(i)=1/n, for each i, then the arithmetic mean is obtained.

Generally speaking, the value of the overall cross-correlation factor $M_{PACE(j)}$ increases in relation to the proximity of the particular pacing electrode Ep(j) to a potential ablation site.

Figure 4B:
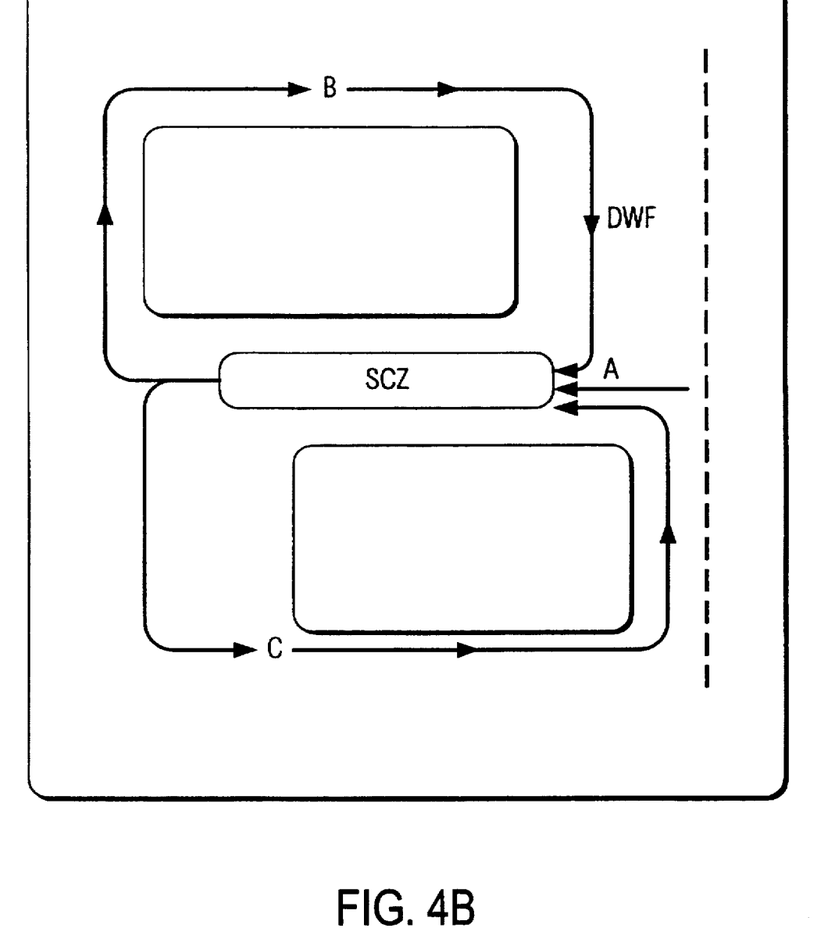
FIG. 4B is a schematic view of a slow conduction zone in myocardial tissue and the circular propagation patterns (called circus motion) it creates.

By way of overall explanation, for VT, the site appropriate for ablation typically constitutes a slow conduction zone, designated SCZ in FIG. 4B. Depolarization wave fronts (designated DWF in FIG. 4B) entering the slow conduction zone SCZ (at site A in FIG. 4B) break into errant, circular propagation patterns (designated B and C in FIG. 4B), called "circus motion." The circus motions disrupt the normal depolarization patterns, thereby disrupting the normal contraction of heart tissue to cause the cardiac event.

The event-specific samples S(i) record these disrupted depolarization patterns. When a pacing signal is applied to a slow conduction zone, the pacing signal gets caught in the same circus motion (i.e., paths B and C in FIG. 4B) that triggers the targeted cardiac event. A large proportion of the associated pacing morphologies P(i) at the sensing electrodes E(i) will therefore cross-correlate with the associated event-specific samples S(i) recorded during the targeted cardiac event. This leads to a greater number of larger cross-correlation coefficients $M_{COEF(i)}$ and thus to a larger overall cross-correlation factor $M_{PACE(j)}$.

However, when a pacing signal is applied outside a slow conduction zone, the pacing signal does not get caught in the same circus motion. It propagates free of circus motion to induce a significantly different propagation pattern than the one recorded in the event-specific samples S(i). A large proportion of the pacing morphologies P(i) at the sensing electrodes E(i) therefore are not well cross-correlated with the event-specific samples S(i). This leads to a smaller number of larger cross-correlation coefficients $M_{COEF(i)}$ and thus to a smaller overall cross-correlation factor $M_{PACE(j)}$.

This is why the overall cross-correlation factor $M_{PACE(j)}$ becomes larger the closer the pacing electrode Ep(j) is to the slow conduction zone, which is the potential ablation site. The difference in propagation patterns between pacing inside and outside a slow conduction zone is particularly pronounced during entrainment pacing. For this reason, entrainment pacing is preferred.

Ablating tissue in or close to the slow conduction zone prevents subsequent depolarization. The destroyed tissue is thereby "closed" as a possible path of propagation. Depolarization events bypass the ablated region and no longer become caught in circus motion. In this way, ablation can restore normal heart function.

Figure 5:
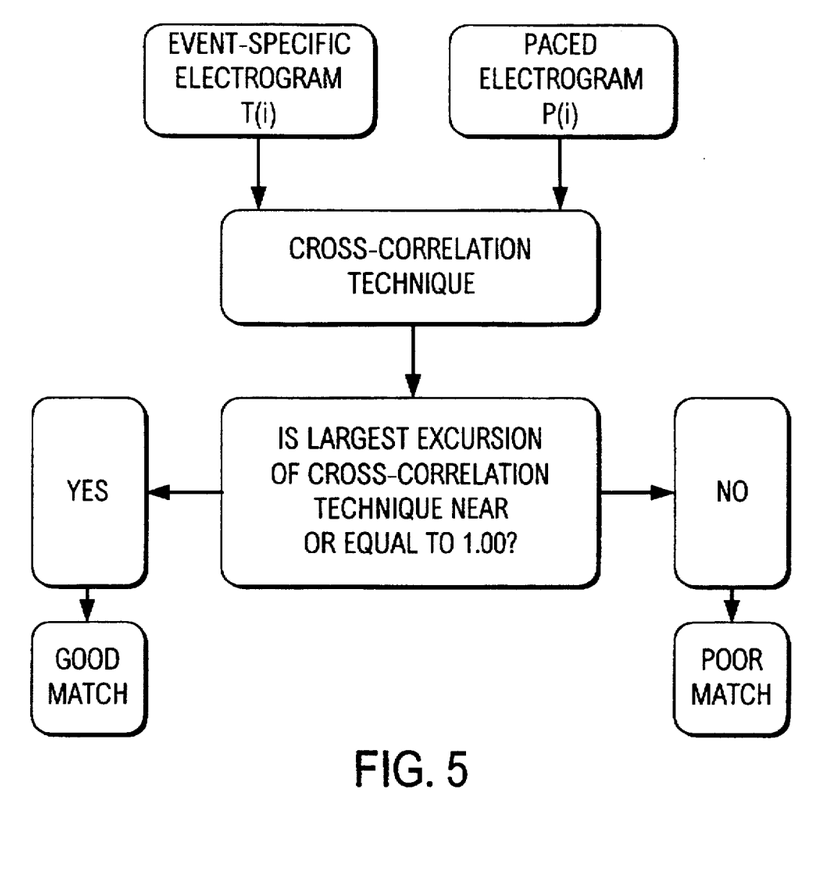
FIG. 5 is a flow chart showing a cross correlation technique that the process controller shown in FIG. 4A can employ for cross-correlating electrograms according to the invention.

The cross-correlation of pacing morphologies P(i) to event-specific samples S(i) to create the coefficient $M_{COEF(i)}$ and the overall factor $M_{PACE(i)}$ can be accomplished using conventional cross correlation techniques. FIG. 5 shows a cross correlation technique that embodies features of the invention.

For example, when the data sequences of the event-specific samples are time aligned with the data sequences of the paced samples, the cross correlation technique can comprise calculating a cross correlation coefficient. For N pairs of time aligned data $\{x(n), y(n)\}$, where x(n) is the event-specific electrogram and y(n) is the paced electrogram, the cross-correlation coefficient can be calculated as follows:

$$rxy = \frac{\sum_{n=1}^{N} [x(n) - \bar{x}][y(n) - \bar{y}]}{\sqrt{\sum_{n=1}^{N} [x(n) - \bar{x}]^2 \Sigma [y(n) - \bar{y}]^2}}$$

Any columnar alignment technique can be used to time align the samples. For example, the electrograms could be aligned about the point of largest positive slope.

$M_{COEF(i)}$ is equal to rxy computed for the individual electrode E(i).

When the data sequences between the eventspecific and paced samples are not time aligned, the cross-correlation technique can comprise calculating a cross-correlation function.

This technique uses an appropriate algorithm to calculate for each electrode a cross correlation function between the event-specific samples of electrogram and the samples of the paced electrograms. For identical electrograms, the largest excursion of the cross correlation function will equal 1.0.

Various conventional methods for determining the cross correlation function can be used. For example, for M pairs of data $\{x(m), y(m)\}$, where x(m) is the event-specific electrogram and y(m) is the paced electrogram, the correlation function can be calculated as follows:

$$rxy(k) = \frac{\Sigma[x(m) - x][y(m+k) - y]}{\sqrt{\Sigma[x(m) - x]^2 \Sigma[y(m) - y]^2}}$$

where m=1 to M; $-M \leq K \leq M$, and x and y are the means of the sequences $\{x\}$ and $\{y\}$.

$M_{COEF(i)}$ is equal to the largest excursion of the sequence $\{rxy(k)\}$ computed for the individual electrode E(i) (i.e., the largest excursion can be either negative or positive, depending upon the degree of intercorrelation).

Figure 6A:
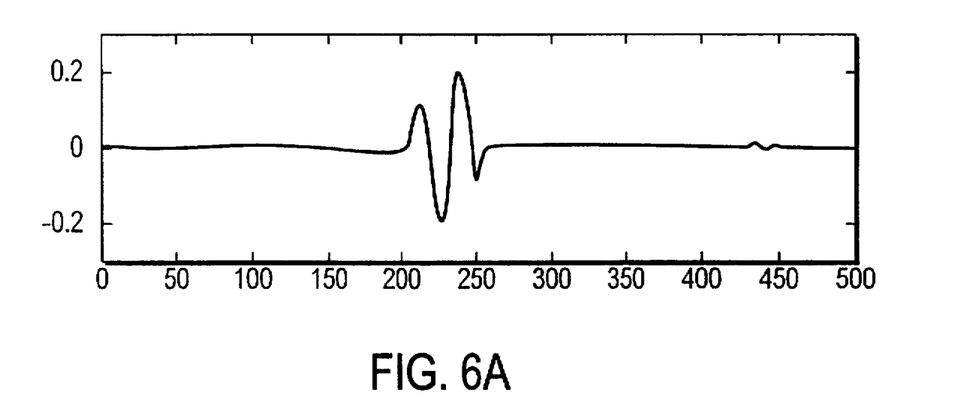
FIGS. 6A and 6B and 6C are representative electrogram morphologies.
Figure 6B:
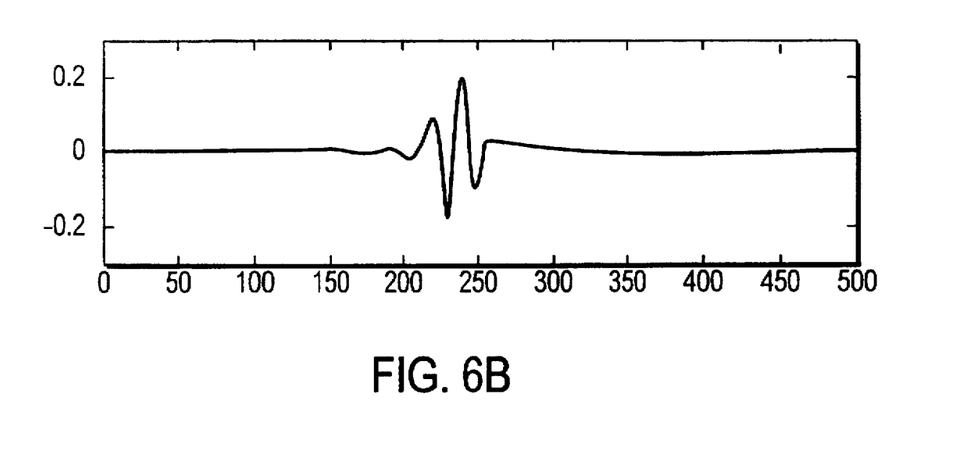
Figure 7A:
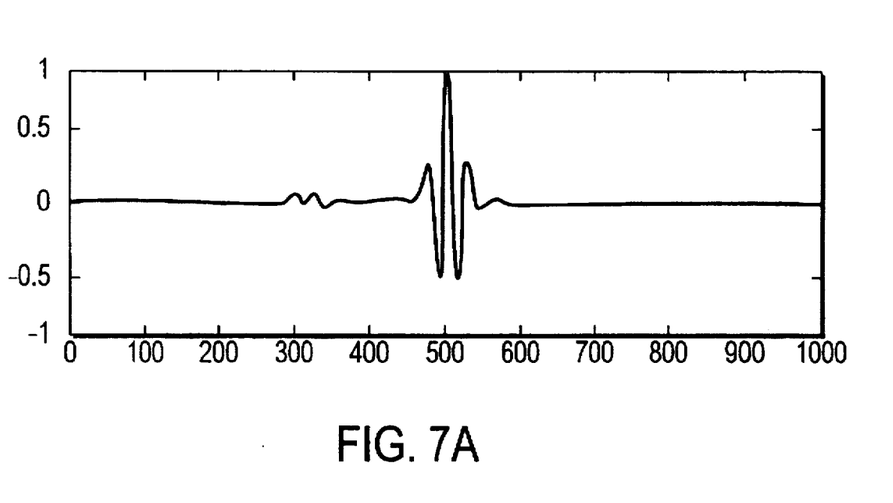
FIG. 7A is the result of cross-correlating the electrogram shown in FIG. 6A with the electrogram shown in FIG. 6B in accordance with the cross correlation coefficient technique shown in FIG. 5.

FIG. 7A shows the cross correlation function for the electrograms of FIG. 6A and FIG. 6B. These electrograms are quite similar, and the cross correlation technique detects this. The largest excursion of the cross correlation function in FIG. 7A is near 1.0 (i.e., it is 0.9694).

Figure 6C:
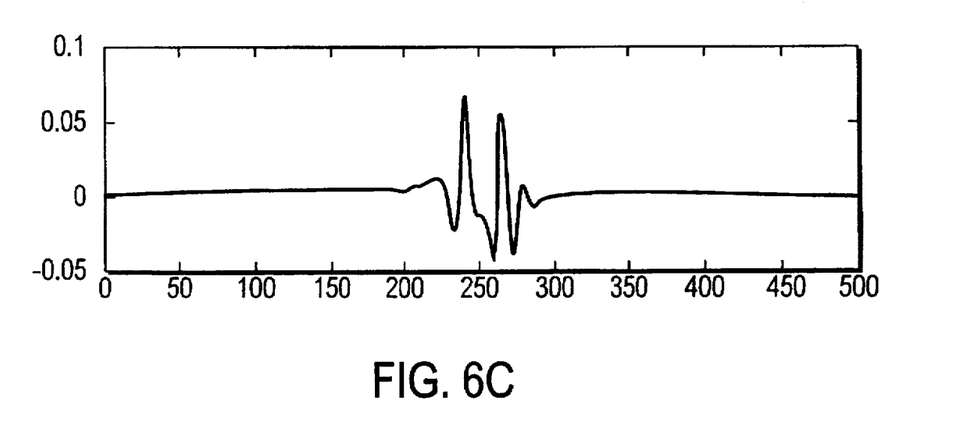
Figure 7B:
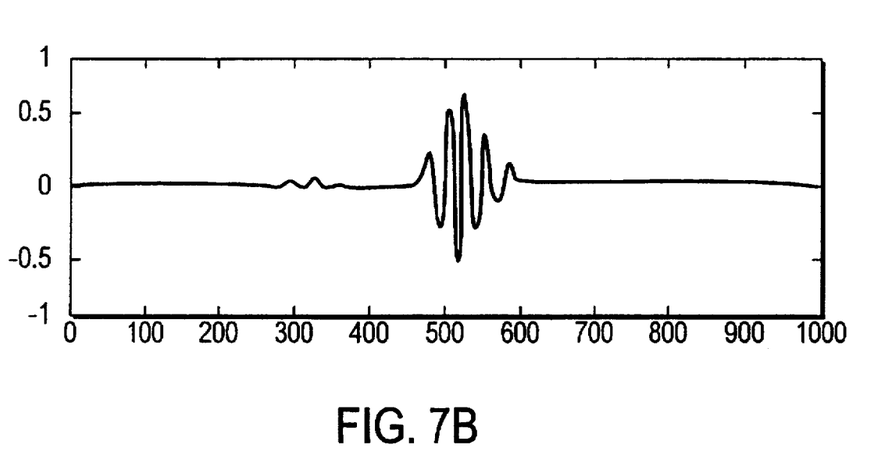
FIG. 7B is the result of cross-correlating the electrogram shown in FIG. 6A with the electrogram shown in FIG. 6C in accordance with the cross correlation coefficient technique shown in FIG. 5.

Refer now to FIG. 7B, which shows the cross correlation function for the unlike electrograms shown in FIGS. 6A and 6C. The cross correlation technique detects this lack of similarity. The largest excursion in FIG. 7B is negative (i.e., it is −0.7191).

Using either a cross-correlation coefficient or a cross-correlation function to calculate $M_{COEF(i)}$, the pacing electrode $Ep(j)$ having an overall factor $M_{PACE(j)}$ closest to 1.0 is designated to be close to a potential ablation site. When using the cross-correlation function technique, additional information may be contained in the shift parameter k for each electrode.

In one implementation (see FIG. 4A), the host processor 52 sets a target N, which numerically establishes a factor $M_{PACE(j)}$ at which a high probability exists that the pacing electrode is close to a potential ablation site. In a preferred implementation, N=0.8. When $M_{ACE(j)} > N$, the host processor 52 deems the location of the pacing electrode $Ep(j)$ to be close to a potential site for ablation. When this occurs (as FIG. 4 shows), the host processor 52 transmits a SITE signal to an associated output display device 54 (see FIG. 1A). Through visual prompts, the display device 54 notifies the physician of the location of the pacing electrode $Ep(j)$ and suggests that location as a potential ablation site.

In the preceding embodiments, the endocardially positioned basket structure 20 both paces and senses the resulting electrograms. In an alternative implementation, the process controller 32 can condition the pacing module 48 in the sampling mode to pace the heart and record resulting electrocardiograms using body surface electrodes electrically coupled to the process controller 32.

In this implementation, during the cross-correlation mode, the process controller 32 paces the heart and records resulting paced electrocardiograms with the same body surface electrodes (located in the same position as during the sampling mode) and compared to the event-specific electrocardiogram samples in the manner above described.

In this implementation, the process controller 32 generates the location output based upon comparing the event-specific electrocardiogram samples with the paced electrocardiograms.

The electrograms may or may not be filtered before analysis. A 1 to 300 Hz bandpass filter may be used for filtering. If a filter is used to reduce the noise for an electrogram that is used as a event-specific sample, the same filter must also be used for the paced electrograms, since filtering may alter the electrogram morphology.

The implementation of the system 10 described herein is based largely upon digital signal processing techniques. However, it should be appreciated that a person of ordinary skill in this technology area can easily adapt the digital techniques for analog signal processing.

Various features of the invention are set forth in the following claims.

We claim:

1. A processing element for analyzing electrograms comprising
   first means for inputting a first number of electrogram samples recorded during a cardiac event of known diagnosis, the first number of electrogram samples comprising a plot of biopotentials over time and not a spacial distribution of endocardial surface activation,
   second means for inputting a second number of paced electrogram samples, the second number of paced electrogram samples comprising a plot of biopotentials over time and not a spacial distribution of endocardial surface activation, and
   third means for cross-correlating the first number of electrogram samples with the second number of paced electrogram samples and generating an output based upon the cross-correlation, whereby the output comprises a diagnostic indicator.

2. An element for analyzing electrocardiograms comprising
   first means for inputting a first number of electrocardiogram samples recorded during a cardiac event of known diagnosis using multiple body surface electrodes, the first number of electrogram samples comprising a plot of biopotentials over time and not a spacial distribution of endocardial surface activation,
   second means for inputting a second number of paced electrocardiogram samples recorded using the multiple body surface electrodes, the second number of paced electrogram samples comprising a plot of biopotentials over time and not a spacial distribution of endocardial surface activation, and
   third means for cross-correlating the first number of electrocardiogram samples with the second number of paced electrocardiogram samples using a cross correlation function and generating an output based upon the cross-correlation function, whereby the output comprises a diagnostic indicator.

3. An element according to claim 1 or 2
wherein the output comprises a numerical cross-correlation function.

4. An element according to claim 1 or 2
wherein the paced samples are triggered from a known pacing site,
and further including fourth means for comparing the output to a predetermined value to determine whether the pacing site is a potential ablation site.

5. An element according to claim 4
wherein the fourth means provides a potential site identification output when the output exceeds the predetermined value.

6. A system for analyzing electrograms comprising
electrode means electrically coupled to myocardial tissue,
a processing element coupled to the electrode means comprising
   first means for conditioning the electrode means to record a first number of electrogram samples during a cardiac event of known diagnosis, the first number of electrogram samples comprising a plot of biopotentials over time and not a spacial distribution of endocardial surface activation.
   second means for conditioning the electrode means to pace the heart and to record with the electrode means a second number of paced electrogram samples, the second number of paced electrogram samples comprising a slot of biopotentials over time and not a spacial distribution of endocardial surface activation, and
   third means for cross-correlating the first number of electrogram samples with the second number of paced electrogram samples and generating an output based upon the cross-correlation whereby the output comprises a diagnostic indicator.

7. A system according to claim 6
wherein the output comprises a numerical cross-correlation function.

8. A system according to claim 6
and further including fourth means for comparing the output to a predetermined value to determine whether the electrode means is near a potential ablation site.

13

9. An element according to claim 8 wherein the fourth means provides a potential site identification output when the output exceeds the predetermined value.

10. A system for analyzing electrograms comprising an array comprising multiple electrodes, an element adapted to support the multiple electrode array within a heart chamber in electrical communication with a region of endocardial tissue, and a processing element coupled to the electrode array comprising first means for conditioning the electrode array to record at each electrode on the array a first number of electrogram samples during a cardiac event of known diagnosis, the first number of electrogram samples comprising a plot of biopotentials over time and not a spacial distribution of endocardial surface activation, second means for conditioning at least one of the multiple electrodes on the array to emit a pacing signal and to record at each electrode a second number of paced electrogram samples, the second number of paced electrogram samples comprising a plot of biopotentials over time and not a spacial distribution of endocardial surface activation, and third means for cross-correlating the first number of electrogram samples with the second number of paced electrogram samples and generating for each electrode on the array an output based upon the cross-correlation, whereby the output comprises a diagnostic indicator.

11. A system according to claim 10 wherein the output for each electrode comprises a numerical cross-correlation function.

12. A system according to claim 10 and further including fourth means for comparing the output to a predetermined value to determine whether the at least one of the multiple electrodes emitting the pacing signal is near a potential ablation site.

13. A system according to claim 12 wherein the fourth means provides a potential site identification output when the output exceeds the predetermined value.

14. A system according to claim 10 wherein the second means sequentially conditions different ones of the multiple electrodes on the array to emit a pacing signal and to record at each electrode on the array the second number of paced electrogram samples for each different one of the pacing signal-emitting electrodes, and wherein the third means individually cross-correlates, for each different one of the pacing signal-emitting electrodes, the first number of electrogram samples with the second number of paced electrogram samples and generates an output for each electrode on the array.

15. A system according to claim 14 wherein the output for each electrode comprises a numerical cross-correlation function.

16. A system according to claim 14 and further including fourth means for comparing each output to a predetermined value to determine whether the pacing signal-emitting electrode is near a potential ablation site.

17. A system according to claim 16 wherein the fourth means provides a potential site identification output when the output exceeds the predetermined value.

14

18. A system for analyzing electrocardiograms comprising multiple body surface electrodes, an element supporting the multiple electrodes in association with a body surface in electrical communication with myocardial tissue, and a processing element coupled to the multiple electrodes comprising first means for conditioning the electrode means to record a first number of electrocardiogram samples during a cardiac event of known diagnosis, the first number of electrocardiogram samples comprising a plot of biopotentials over time and not a spacial distribution of endocardial surface activation, second means for conditioning the multiple electrodes to pace the heart and to record with the electrodes a second number of paced electrocardiogram samples, the second number of paced electrocardiogram samples comprising a plot of biopotentials over time and not a spacial distribution of endocardial surface activation, and third means for cross-correlating the first number of electrocardiogram samples with the second number of paced electrocardiogram samples and generating an output based upon the cross-correlation whereby the output comprises a diagnostic indicator.

19. A system according to claim 18 wherein the output for each electrode comprises a numerical cross-correlation function.

20. A system according to claim 18 and further including fourth means for comparing the output to a predetermined value to determine whether the electrode means pacing the heart is near a potential ablation site.

21. A system according to claim 20 wherein the fourth means provides a potential site identification output when the output exceeds the predetermined value.

22. A system according to claim 18 wherein the second means sequentially conditions different ones of the multiple electrodes to emit a pacing signal and to record at each electrode the second number of paced electrocardiogram samples for each different one of the pacing signal-emitting electrodes, and wherein the third means individually cross-correlates, for each different one of the pacing signal-emitting electrodes, the first number of electrocardiogram samples and the second number of paced electrocardiogram samples recorded by each electrode and generates an output associated with each electrode.

23. A system according to claim 22 wherein the output for each electrode comprises a numerical cross-correlation function.

24. A system according to claim 22 and further including fourth means for comparing each output to a predetermined value to determine whether the electrode means pacing the heart is near a potential ablation site.

25. A system according to claim 24 wherein the fourth means provides a potential site identification output when the output exceeds the predetermined value.

26. A method for analyzing electrograms comprising the steps of inputting a first number of electrogram samples recorded during a cardiac event of known diagnosis, the first number of electrogram samples comprising a plot of biopotentials over time and not a spacial distribution of endocardial surface activation.

inputting a second number of paced electrogram samples, the second number of paced electrogram samples comprising a plot of biopotentials over time and not a spacial distribution of endocardial surface activation, and cross-correlating the first number of electrogram samples with the second number of paced electrogram samples and generating an output based upon the cross-correlation, whereby the output comprises a diagnostic indicator.

27. A method according to claim 26 and further including the step of comparing the output to a predetermined value to determine whether a pacing site for the paced electrogram samples is near to a potential ablation site.

28. A method according to claim 27 wherein the step of comparing the output to a predetermined value provides a potential site identification output when the output exceeds the predetermined value.

29. A method for analyzing electrograms comprising the steps of conditioning an array of multiple electrodes supported within a heart chamber in electrical communication with a region of endocardial tissue to record at each electrode on the array a first number of electrogram samples during a cardiac event of known diagnosis, the first number of electrogram samples comprising a plot of biopotentials over time and not a spacial distribution of endocardial surface activation.

conditioning at least one of the multiple electrodes on the array to emit a pacing signal and to record at each electrode a second number of paced electrogram samples, the second number of paced electrogram samples comprising a plot of biopotentials over time and not a spacial distribution of endocardial surface activation, and cross-correlating the first number of electrogram samples with the second number of paced electrogram samples and generating for each electrode on the array an output based upon the cross-correlation, whereby the output comprises a diagnostic indicator.

30. A method according to claim 29 and further including the step of comparing the output to a predetermined value to determine whether a pacing site for the paced electrocardiogram samples is near to a potential ablation site.

31. A method according to claim 30 wherein the step of comparing the output to a predetermined value provides a potential site identification output when the output exceeds the predetermined value.

32. A method for analyzing electrocardiograms comprising the steps of inputting a first number of electrocardiogram samples recorded during a cardiac event of known diagnosis using multiple body surface electrodes in electrical communication with myocardial tissue, the first number of electrocardiogram samples comprising a plot of biopotentials over time and not a spacial distribution of endocardial surface activation.

inputting a second number of paced electrocardiogram samples recorded using the multiple body surface electrodes, the second number of paced electrocardiogram samples comprising a plot of biopotentials over time and not a spacial distribution of endocardial surface activation, and cross-correlating the first number of electrocardiogram samples with the second number of paced electrocardiogram samples and generating an output based upon the cross-correlation, whereby the output comprises a diagnostic indicator.

33. A method according to claim 32 and further including the step of comparing the output to a predetermined value to determine whether a pacing site for the paced electrocardiogram samples is near to a potential ablation site.

34. A method according to claim 33 wherein the step of comparing the output to a predetermined value provides a potential site identification output when the output exceeds the predetermined value.

35. A method for analyzing electrocardiograms in myocardial tissue comprising the steps of conditioning multiple body surface electrodes in association with a body surface in electrical communication with myocardial tissue to record a first number of electrocardiogram samples during a cardiac event of known diagnosis, the first number of electrocardiogram samples comprising a slot of biopotentials over time and not a spacial distribution of endocardial surface activation, conditioning electrode means to pace the heart and to record with the multiple body surface electrodes a second number of paced electrocardiogram samples, the second number of paced electrocardiogram samples comprising a plot of biopotentials over time and not a spacial distribution of endocardial surface activation, and cross-correlating the first number of electrocardiogram samples with the second number of paced electrocardiogram samples and generating an output based upon the cross-correlation, whereby the output comprises a diagnostic indicator.

36. A method according to claim 35 and further including the step of comparing the output to a predetermined value to determine whether a pacing site for the paced electrocardiogram samples is near to a potential ablation site.

37. A method according to claim 36 wherein the step of comparing the output to a predetermined value provides a potential site identification output when the output exceeds the predetermined value.

38. A method according to claim 26 or 29 or 32 or 35 wherein the output comprises a numerical cross-correlation function.

* * * * *